United States Patent
Cornsweet et al.

(10) Patent No.: US 7,360,895 B2
(45) Date of Patent: Apr. 22, 2008

(54) SIMPLIFIED OCULAR FUNDUS AUTO IMAGER

(75) Inventors: Tom N. Cornsweet, Prescott, AZ (US); Gary F. Buck, Prescott, AZ (US); Paul R. Peterson, Prescott, AZ (US)

(73) Assignee: Visual Pathways, Inc., Prescott, AZ (US)

( * ) Notice: Subject to any disclaimer, the term of this patent is extended or adjusted under 35 U.S.C. 154(b) by 382 days.

(21) Appl. No.: 10/867,523

(22) Filed: Jun. 14, 2004

(65) Prior Publication Data

US 2004/0263784 A1 Dec. 30, 2004

Related U.S. Application Data

(63) Continuation-in-part of application No. 10/311,492, filed as application No. PCT/US01/21410 on Jul. 6, 2001, now Pat. No. 7,025,459, which is a continuation of application No. 09/649,462, filed on Aug. 25, 2000, now Pat. No. 6,296,358.

(60) Provisional application No. 60/218,757, filed on Jul. 17, 2000.

(51) Int. Cl.
*A61B 3/14* (2006.01)

(52) U.S. Cl. .................................... 351/206

(58) Field of Classification Search ............... 351/205, 351/206, 208, 210, 213, 214, 216, 218, 246, 351/223

See application file for complete search history.

(56) References Cited

U.S. PATENT DOCUMENTS

| | | | |
|---|---|---|---|
| 3,915,564 A | 10/1975 | Urban | 351/7 |
| 4,019,813 A | 4/1977 | Cornsweet et al. | 351/14 |
| 4,187,014 A | 2/1980 | Kato et al. | 354/62 |
| 4,281,926 A | 8/1981 | Cornsweet | 356/124 |
| 4,283,124 A | 8/1981 | Matsumura | 351/7 |
| 4,329,049 A | 5/1982 | Rigg et al. | 356/124 |
| 4,405,215 A | 9/1983 | Sano et al. | 351/208 |
| 4,436,388 A | 3/1984 | Takahashi et al. | 351/206 |
| 4,469,416 A | 9/1984 | Isono | 351/206 |
| 4,526,450 A | 7/1985 | Suzuki et al. | 351/206 |
| 4,544,248 A | 10/1985 | Nunokawa | 354/62 |
| 4,579,430 A | 4/1986 | Bille | 351/206 |
| 4,580,885 A | 4/1986 | Takahashi | 354/62 |
| 4,591,249 A | 5/1986 | Takahashi et al. | 354/62 |
| 4,666,268 A | 5/1987 | Ito | 351/206 |
| 4,673,264 A | 6/1987 | Takahashi | 351/211 |
| 4,690,525 A | 9/1987 | Kobayashi et al. | 351/206 |
| 4,715,703 A * | 12/1987 | Cornsweet et al. | 351/205 |
| 4,732,466 A | 3/1988 | Humphrey | 351/206 |
| 4,773,749 A | 9/1988 | Ohtomo et al. | 351/206 |

(Continued)

FOREIGN PATENT DOCUMENTS

WO WO96/17545 12/1995

*Primary Examiner*—M. Hasan
(74) *Attorney, Agent, or Firm*—Cahill, von Hellens & Glazer, PLC (57) ABSTRACT

An ocular fundus imager automatically aligns fundus illuminating rays to enter the pupil and to prevent corneal reflections from obscuring the fundus image produced. Focusing the produced fundus image is automatically performed using a pair of video sensors and is based upon the fundus image itself. A head restraint is used to reduce the gross alignment between the optical system and the patient's pupil.

23 Claims, 8 Drawing Sheets

U.S. PATENT DOCUMENTS

| | | | |
|---|---|---|---|
| 4,834,526 A | 5/1989 | Nunokawa | 351/206 |
| 4,902,121 A | 2/1990 | Shinn | 351/208 |
| 4,989,023 A | 1/1991 | Sakurai et al. | 354/62 |
| 4,993,827 A | 2/1991 | Benedek et al. | 351/221 |
| 5,064,286 A | 11/1991 | Ai et al. | 356/153 |
| 5,072,731 A | 12/1991 | Taratuta et al. | 128/633 |
| 5,090,799 A | 2/1992 | Makino et al. | 351/221 |
| 5,114,222 A | 5/1992 | Cornsweet | 351/204 |
| 5,125,730 A | 6/1992 | Taylor et al. | 351/206 |
| 5,129,400 A | 7/1992 | Makino et al. | 128/666 |
| 5,196,872 A | 3/1993 | Beesmer et al. | 351/208 |
| 5,202,708 A | 4/1993 | Sasaki et al. | 351/206 |
| 5,210,554 A | 5/1993 | Cornsweet et al. | 351/206 |
| 5,233,517 A | 8/1993 | Jindra | 364/413.13 |
| 5,349,419 A | 9/1994 | Taguchi et al. | 355/22 |
| 5,371,557 A | 12/1994 | Nanjho et al. | 351/206 |
| 5,382,988 A | 1/1995 | Nanjo | 351/206 |
| 5,410,376 A | 4/1995 | Cornsweet et al. | 351/210 |
| 5,422,690 A | 6/1995 | Rothberg et al. | 351/209 |
| 5,504,543 A | 4/1996 | Ueno | 351/206 |
| 5,508,760 A | 4/1996 | Kobayashi et al. | 351/221 |
| 5,539,487 A | 7/1996 | Taguchi et al. | 354/115 |
| 5,540,226 A | 7/1996 | Thurston et al. | 128/633 |
| 5,542,422 A | 8/1996 | Hayden | 128/633 |
| 5,572,266 A | 11/1996 | Ohtsuka | 396/18 |
| 5,579,063 A | 11/1996 | Magnante et al. | 351/211 |
| 5,697,006 A | 12/1997 | Taguchi et al. | 396/330 |
| 5,710,630 A | 1/1998 | Essenpreis et al. | 356/345 |
| 5,713,047 A | 1/1998 | Kohayakawa | 396/18 |
| 5,764,341 A | 6/1998 | Fujieda et al. | 351/221 |
| 5,844,658 A | 12/1998 | Kishida et al. | 351/206 |
| 5,896,198 A | 4/1999 | Chou et al. | 356/349 |
| 5,908,394 A | 6/1999 | Kandel et al. | 600/558 |
| 5,912,720 A | 6/1999 | Berger et al. | 351/206 |
| 5,914,771 A | 6/1999 | Biber | 351/221 |
| 5,943,116 A | 8/1999 | Zeimer | 351/221 |
| 5,993,001 A | 11/1999 | Bursell et al. | 351/212 |
| 6,086,205 A | 7/2000 | Svetliza | 351/221 |
| 6,112,114 A | 8/2000 | Dreher | 600/476 |
| 6,179,421 B1 | 1/2001 | Pang | 351/205 |
| 6,257,722 B1 | 7/2001 | Toh | 351/208 |
| 6,276,799 B1 | 8/2001 | Van Saarloos | 351/206 |
| 6,296,358 B1 * | 10/2001 | Cornsweet et al. | 351/206 |
| 6,304,723 B1 * | 10/2001 | Kohayakawa | 396/18 |
| 6,309,068 B1 | 10/2001 | Kohayakawa | 351/221 |
| 6,361,167 B1 | 3/2002 | Su et al. | 351/206 |
| 6,659,613 B2 | 12/2003 | Applegate et al. | 351/221 |

* cited by examiner

FIG. 2b TOP VIEW

FIG. 2a VIEW FROM PATIENT'S EYE SIDE

SIMPLIFIED OCULAR FUNDUS AUTO IMAGER

CROSS REFERENCE TO RELATED APPLICATIONS

The present application is a continuation-in-part application of an application entitled "Ocular Fundus Auto Imager", filed Dec. 16, 2002, assigned Ser. No. 10/311,492, now U.S. Pat. Ser. No. 7,025,459 which is a national phase application based on a Patent Cooperation Treaty application entitled "Ocular Fundus Auto Imager", filed Jul. 6, 2001, assigned Ser. No. PCT/US01/21410, which is a continuation of and claims priority to a United States application entitled "Ocular Fundus Auto Imager", filed Aug. 25, 2000, assigned Ser. No. 09/649,462, now U.S. Pat. No. 6,296,358 and which application claims priority to the subject matter disclosed in a provisional application entitled "FUNDUS AUTO IMAGER", filed Jul. 17, 2000 and assigned Ser. No. 60/218,757 all of which applications are directed to an invention made by the present inventors and assigned to the present assignee.

BACKGROUND OF THE INVENTION

1. Field of the Invention

The present invention relates to the field of ocular imaging, and, more particularly, to devices for imaging the ocular fundus.

2. Description of Related Art

The term ocular fundus refers to the inside back surface of the eye containing the retina, blood vessels, nerve fibers, and other structures. The appearance of the fundus is affected by a wide variety of pathologies, both ocular and systemic, such as glaucoma, macular degeneration, diabetes, and many others. For these reasons, most routine physical examinations and virtually all ophthalmic examinations include careful examination of the ocular fundus.

Routine examination of the ocular fundus (hereinafter referred to as fundus) is performed using an ophthalmoscope, which is a small, hand-held device that shines light through the patient's pupil to illuminate the fundus. The light reflected from the patient's fundus enters the examiner's eye, properly focused, so that the examiner can see the fundus structures.

If a hard copy of the fundus view is desired, a device called a fundus camera can be used. However, to use existing fundus cameras successfully is a very difficult undertaking. The operator must (1) position the fundus camera at the correct distance from the eye, (2) position it precisely in the vertical and horizontal directions in such a way that the light properly enters the pupil of the patient's eye, (3) refine the horizontal and vertical adjustments so that the light reflected from the front surface of the eye, the cornea, does not enter the camera, (4) position a visual target for the patient to look at so that the desired region of the fundus will be imaged, and (5) focus the fundus image. All these operations must be performed on an eye that is often moving. Therefore, the use of existing fundus cameras requires a significant amount of training and skill; even the most skilled operators often collect a large number of images of a single eye in order to select one that is of good quality.

In existing fundus cameras, alignment and focusing are performed under visual control by the operator. This usually requires that the patient's eye be brightly illuminated. Such illumination would normally cause the pupils to constrict to a size too small to obtain good images. Therefore, most existing fundus cameras require that the patient's pupil be dilated by drugs.

U.S. Pat. No. 4,715,703 describes an invention made by one of the present inventors and discloses apparatus for analyzing the ocular fundus. The disclosure in this patent is incorporated herein by reference.

SUMMARY OF THE INVENTION

The present invention is in the nature of a fundus camera which automatically and quickly performs all the aligning and focusing functions. As a result, any unskilled person can learn to obtain high quality images after only a few minutes of training and the entire imaging procedure requires far less time than existing fundus cameras. Moreover, all of the automatic aligning and focusing procedures are performed using barely visible infrared illumination. With such illumination, the patient's pupils do not constrict and for all but patients with unusually small natural pupils, no artificial dilation is required. The fundus images can be obtained under infrared illumination and are acceptable for many purposes so that the patient need not be subjected to the extremely bright flashes required for existing fundus cameras. To obtain standard color images using the present invention, it is sometimes necessary to illuminate the eye with flashes of visible light. However, such images can be obtained in a time appreciably shorter than the reaction time of the pupil, so that the pupil constriction that results from the visible flash does not interfere with image collection. Unlike existing fundus cameras, the present invention provides for automatic selection of arbitrary wavelengths of the illuminating light. This facility has two significant advantages. First, it is possible to select illuminating wavelengths that enhance the visibility of certain fundus features. For example, certain near-infrared wavelengths render the early stages of macular degeneration more visible than under white illumination. Second, by careful selection of two or more wavelengths in the near infrared, it is possible to obtain a set of images which, when properly processed, generate a full color fundus image that reveals sub-retinal fundus features. Thus, it is possible to obtain acceptable color fundus images without subjecting the patient to bright flashes.

It is therefore a primary object of the present invention to provide a fundus imager which automatically positions fundus illuminating radiation to enter the pupil while preventing reflection from the cornea from obscuring the fundus image, irrespective of movement of the eye or the patient's head within the head restraint.

Another object of the present invention is to provide automatic focusing of the fundus image based upon the image itself.

Yet another object of the present invention is to provide automatic positioning of one or a sequence of fixation targets to select the sections(s) of the fundus to be imaged.

Still another object of the present invention is to provide a fundus imager for collecting a set of images that can be arranged in a montage to provide a very wide angle fluids image facilitated by the capability of the fundus imager to automatically align and focus the images.

A further object of the present invention is to provide automatic setting of video levels in a fundus imager to use the full range of levels available.

Yet another object of the present invention is to permit aligning and focusing a fundus imager under infrared illumination to permit imaging without drug induced dilation of the pupil.

A yet further object of the present invention is to provide for automatic selection of illumination wavelength.

A yet further object of the present invention is to provide a colored image from a fundus imager by sequential imaging and registration of images.

A yet further object of the present invention is to provide for automatic acquisition by a fundus imager of a stereo image pair having a known stereo base.

A yet further object of the present invention is to provide a head positioning frame for use with a fundus imager.

A yet further object of the present invention is to accommodate for astigmatism and/or extreme near and far sightedness by placing a lens of the patient's glasses in the path of illumination of the fundus imager.

A yet further object of the present invention is to provide a method for automatically positioning the illuminating radiation of a fundus imager to prevent corneal reflections from obscuring the fundus image obtained.

A yet further object of the present invention is to provide a method for automatic focusing in a fundus imager.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is a schematic diagram illustrating the functional elements of the present invention and FIG. 1 a representatively illustrates structure for moving the optical system;

DESCRIPTION OF THE PREFERRED EMBODIMENT

Figures 1, 1A:
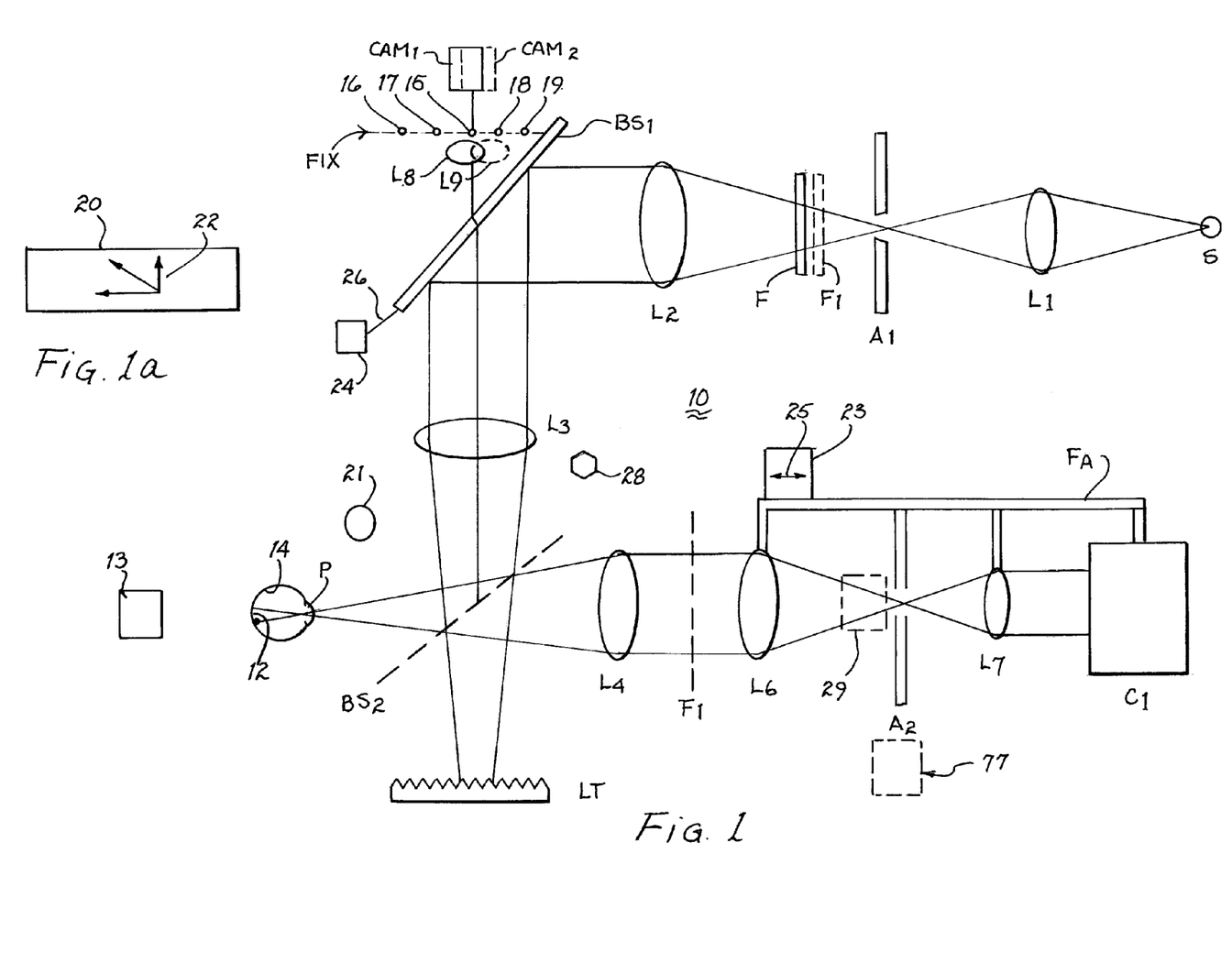

Referring to FIG. 1, there is illustrated a preferred embodiment of optical system 10 of the present invention. Lens L1 focuses light from a light source S onto a small aperture A1. The light source may be a source of visible light, infrared radiation or of a wavelength in the near visible infrared region. Light passing through aperture A1 passes through a filter F toward lens L2. Lens L2 collimates (makes parallel) light from aperture A1. A beam splitter BS1 reflects about ninety percent (90%) of the incident light from lens L2 to lens L3. Half of the light passing through lens L3 is transmitted through beam splitter BS2 and is absorbed by light trap LT. The other half of the light passing through lens L3 is reflected by beam splitter BS2 and forms an image of aperture A1 in the focal plane of lens L3, which focal plane lies in the plane of a patient's pupil P. The light passing through the pupil illuminates a section 12 of ocular fundus 14 (hereinafter only the term fundus will be used).

Light diffusely reflected from fundus 14 emerges from pupil P and half of it is transmitted through beam splitter BS2 toward collimating lens L4, which lens is at its focal distance from the pupil. If the patient's eye is focused at infinity, the light reflected from each point on fundus 14 will be collimated as it is incident on lens L4. Therefore, the 50% of the light that passes through beam splitter BS2 will form an aerial image of the fluids in the focal plane of lens L4, which focal plane is represented by a dashed line identified as FI (Fundus Image). The light passes through lens L6, which lens is at its focal distance from fundus image FI. Thus, lens L6 will collimate light from each point on the fundus. Further, because the light considered as originating in the plane of pupil P is collimated by lens L4, lens L6 will form an image of the pupil in its back focal plane, which is coincident with the location of second aperture A2. Light passing through second aperture A2 is incident on lens L7, which lens will then form an image of the fundus in its back focal plane which is coincident with an image sensor or video sensor C1. The video image produced by video sensor C1 represents an image of the fluids.

An infrared light emitting diode (LED), representatively shown and identified by reference numeral 21, diffusely illuminates the region of the front of the eye.

If the eye is not focused at infinity, the aerial fundus image FI will be moved away from the back focal plane of lens L4. For example, if the eye is nearsighted, the aerial fundus image will move toward lens L4. Such movement would cause the fundus image to be defocused on video sensor C1. Focusing the image under these conditions is accomplished as follows. Lens L6, aperture A2, lens L7, and video sensor C1 are mechanically connected to one another by a focusing assembly labeled FA; that is, these elements are fixedly positioned relative to one another and move as a unit upon movement of the focusing assembly. A unit identified by reference numeral 23 provides rectilinear movement of the focusing assembly on demand.

The entire optical system (10) discussed above and illustrated in FIG. 1 is supported upon an assembly shown in FIG. 1a and identified by reference numeral 20. The assembly includes motive elements, such as rectilinear actuators and related servomechanisms responsive to commands for translating the entire optical system horizontally (laterally), vertically and toward and away from the eye, or movement in the x, y and z axis as representatively depicted by set of arrows 22. By moving the assembly as necessary in the x, y and z axis the illumination light is positioned on the eye.

Figure 3:
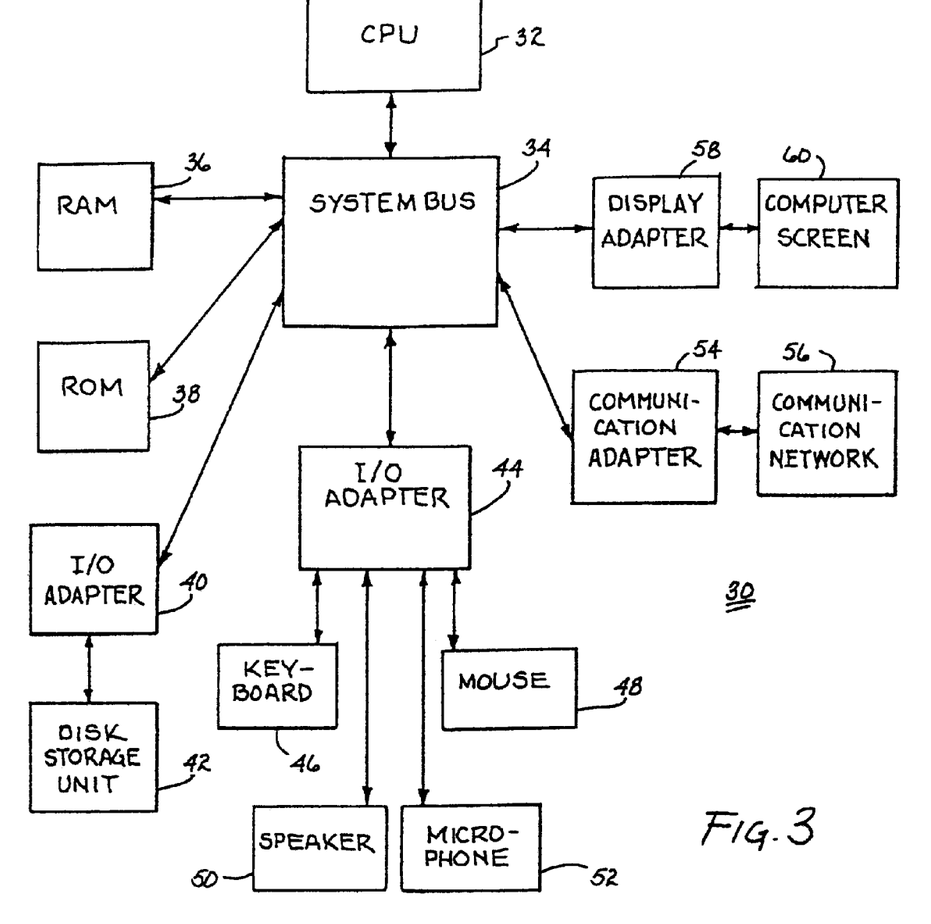
FIG. 3 is a block diagram illustrating a representative computer system for operating the present invention.

To operate optical system 10, a computer control system 30 is required, which is representatively illustrated in FIG. 3. The computer control system includes a central processing unit (CPU) 32, such as a microprocessor, and a number of units interconnected via a system bus 34. A random access memory (RAM) 36, a read only memory (ROM) 38 are incorporated. An input/output adapter 40 interconnects peripheral devices, such as a disk storage unit 42. A user interface adapter 44 connects the keyboard 46, a mouse (or trackball) 48, a speaker 50, a microphone 52, and/or other user interface devices, such as a touch screen (not shown) with system bus 34. A communication adapter 54 interconnects the above described optical system 10 through a communication network 56. A display adapter 58 interconnects a display unit 60, which maybe a video screen, monitor, or the like. The computer operating system employed maybe any one of presently commercially available operating systems.

In operation, an operator enters patient information data into the computer control system using the keyboard and also enters the location or set of locations on the fluids that is/are to be imaged. It may be noted that the field of view of the optical system is preferably 30° in diameter while the ocular fundus is about 200° in diameter. To image various regions of the 200° fundus, the eye can be rotated with respect to the optical system; such rotation is achieved by having the patient look from one reference point to another. After entry of the raw data, the patient's head is juxtaposed with a head positioning apparatus to locate the eye in approximate alignment with respect to the optical axis. An image of the front of the eye produced by a video sensor or camera CAM, (FIG. 1) appears on computer-screen 60. The operator may use a trackball or mouse 48 or similar control to move the image horizontally and vertically until the pupil is approximately centered on a set of cross-hairs displayed on the computer screen. Such horizontal and vertical movements, along with focusing of the image of the pupil, are achieved by moving entire optical system 10 through energization of assembly 20 (see FIG. 1). That is, the horizontal and vertical movements of the image are achieved by moving the entire optical system horizontally and vertically and the focusing of the pupil image is accomplished by moving the entire optical system toward or away from the eye. When the operator is satisfied that the pupil is approximately centered, the operator de-energizes LED 21 (which illuminated the front of the eye) and then initiates the automatic alignment and image collection procedure.

To achieve proper alignment of the optical system with the eye requires that the light from light source S enter the pupil. Initially, the angular position of beam splitter BS1 is set so that the image of aperture A1 lies on the optical axis of the system. It is noted that the image of aperture A1 contains the light used to illuminate the ftndus. If the operator has initially centered the pupil image even crudely, light from light source S will enter the pupil. About two percent (2%) of the light incident on the eye will be reflected from the corneal surface and if this light reaches video sensor C1, it would seriously obscure the image of the fundus. Therefore, the optical system includes the following elements for preventing corneal reflection from reaching video sensor C1.

Figure 4:
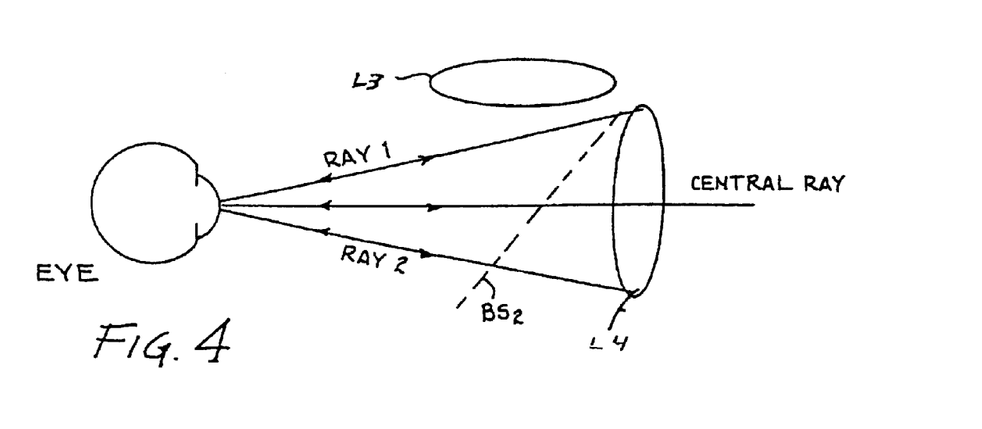
FIG. 4 illustrates the effect of corneal reflections to be avoided.

If the light rays forming the image of aperture A1 were aligned so that the central ray were perpendicular to the corneal surface, then many of the rays in the corneal reflection would pass backward along the incident light paths. As shown in FIG. 4, the central ray would pass back on itself; the ray labeled Ray-1 would pass back along the path of the incident ray labeled Ray-2, etc. (The angle at which a ray is reflected from a shiny surface can be determined as follows. First, find the line that is perpendicular to the surface at the point that the ray hits. Then find the angle between the incident ray and the perpendicular ray; this is called the "angle of incidence". Finally, the ray will be reflected at an angle equal to the angle of incidence but on the other side of the perpendicular line. This is called the angle of reflection.) It is therefore evident from the schematic shown in FIG. 4 that many rays reflected from the corneal surface and impinging upon beam splitter BS2 would enter lens L4 and impinge upon video sensor C1.

Figure 5:
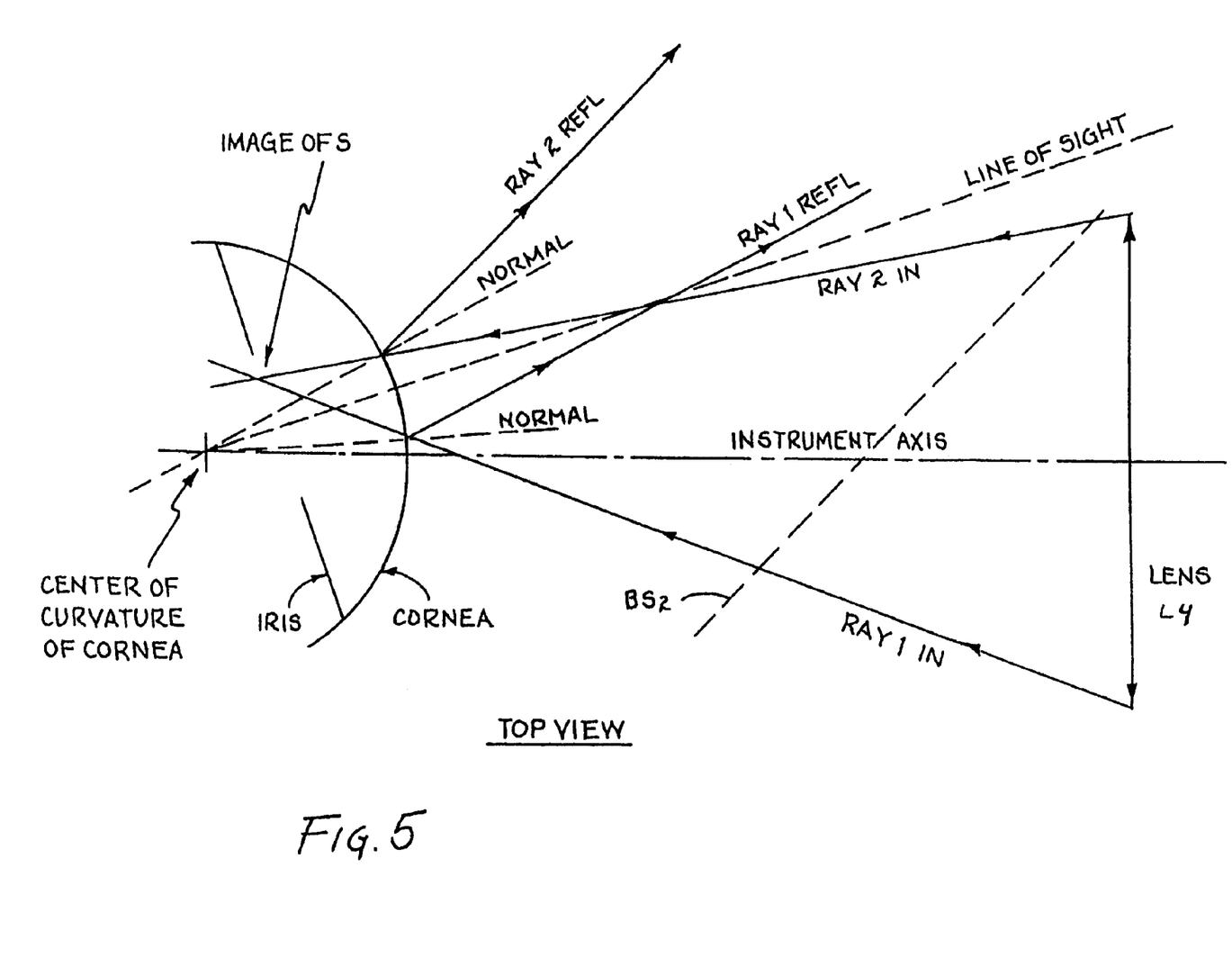
FIG. 5 is a schematic illustrating an alignment of the optical axis to avoid corneal reflections.

However, the corneal surface is steeply curved and if the central ray of the incident light is moved far enough away from the perpendicular to the cornea, as shown in FIG. 5, the reflected light will be deflected far enough to miss beam splitter BS2 and therefore miss passing through lens L4 and therefore not impinge upon video sensor C1. The method for achieving this deflection will be described below.

Initially, the angle of beam splitter BS1 (FIG. 1) is set so that the image of A1 lies on the optical axis. Thereby, the optical system is automatically aligned to be centered on the pupil and the image of A1 is in the plane of the pupil, as set forth below. When this alignment is accomplished, the image A1 will be centered on and in focus in the plane of the pupil.

If a fundus image were to be collected under these conditions, the reflection from the cornea would severely spoil the fundus image. To prevent this, after alignment is achieved, the angular position of beam splitter BS1 is changed by motor 24 and linkage 26 to move the image of A1 to the bottom of the pupil. If the pupil is about 4mm or larger in diameter, this will deflect the corneal reflection sufficiently that it will not enter lens L4. To do this, the diameter of the pupil must be known. This diameter is determined by performing the method described below for automatic alignment in the vertical and horizontal directions.

If the pupil is relatively small, a further technique is employed to allow greater displacement of the illumination away from the center of the pupil. This is accomplished by automatically changing the aiming point of the vertical alignment servo so that the image of the pupil moves downward with respect to the optical axis by an amount that is a fixed proportion of the pupil diameter. Thus, the regions of the pupil through which the images are collected moves toward the top of the pupil and the image of A1 has more room to move downward. This description refers to movement of the image of A1 to the bottom of the pupil. The same effect can be achieved by moving the bar to the top of the pupil and moving the servo aiming point so that the pupil image moves upward. In general, if the patient is looking downward, moving the image of A1 downward is more effective and if the patient is looking upward, it is more effective to move the image of A1 to the top of the pupil.

A method for tracking the pupil and positioning the image of aperture A1 on the pupil of the eye will be described hereafter with reference to FIG. 1. The images appearing on video sensors or cameras $CAM_1$ and $CAM_2$ are used for automatic tracking of the eye and the positioning of the image of aperture A1. This is done by using the computer system and its software for extracting the edges of the pupil from the video signal and computing the coordinates of its center and of its edges.

About half of the light reflected from fundus 14 is reflected from beam splitter BS2 through lens L3, and about 10% of that light passes through beam splitter BS1. Some of that light passes through a lens L8 and falls on a small camera $CAM_1$ on which an image of the pupil is formed. Others of those rays pass through another lens L9 (shown in dashed lines) and to camera $CAM_2$ (shown in dashed lines) and forms another image of the pupil. These lenses and cameras are placed one above and the other below the plane of the paper in FIG. 1. Thereby, one camera receives the image of the pupil as seen at an angle to the left of the optical axis and the other camera receives the image of the pupil as seen at an angle to the right of the optical axis.

The output of one of these cameras is used to position optical system 10 in the x and y axis, as described in further detail below. To position the optics at the correct distance from the eye (the z direction), the images from cameras $CAM_1$ and $CAM_2$ are compared in software. When the pupil is at the correct distance from the optics, that is, when the pupil is in the focal plane of lens L3 (and therefore, because of the mechanical arrangement, in the focal plane of lens L4), then the two pupil images will lie in a particular relationship to each other. If the optical system were perfectly aligned and centered, the two images would each be perfectly centered in the fields of view of their respective cameras $CAM_1$ and $CAM_2$. Then, considering the fields of view of the two cameras as superimposed, if the pupil image from the left camera is to the left of the image from the right camera, then the optics need to be moved closer to the patient and vice versa.

If the optical system is not perfectly aligned, there will be a particular relative positioning between the two images that occurs when the pupil is in the correct position, and the software drives optical system 10 in the z direction until that relative position is attained. (That relative position is determined during the procedure for optically aligning the entire system.)

Figure 6:
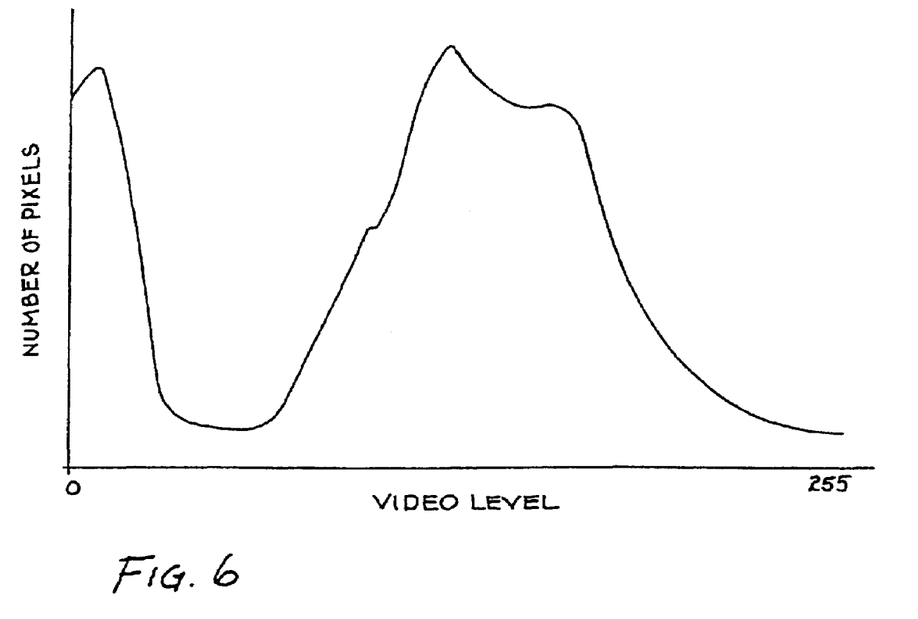
FIGS. 6 is a graph illustrating determination of an acceptable video level.

A method for finding the center and the edges of the pupil image will now be described. It involves finding the edges of the pupil image on each video line that intersects the edges and then computing the most likely position of the center and of the edges of the actual pupil. The image from camera $CAM_1$ is read out, as is the standard video practice, by reading the values of the various points along a horizontal line and then the values along the next horizontal line, etc. (neglecting the detail of interlacing). If a given video horizontal line intercepts the image of the pupil, the video level will abruptly rise from the dark background level to the brighter level of the pupil. To locate this transition and find the position of each edge, it is necessary to define the values of the background and of the pupil. To do this, a histogram of pixel values is formed during the first few video frames. It will contain a large peak with values near zero, representing dark background pixels, and additional peaks at higher values that represent the pupil and various reflections to be discussed below. A typical histogram is illustrated in FIG. 6. Each point along the horizontal axis represents a different video signal level and each point on the vertical axis indicates the area of the image that displays the corresponding video level.

The "background level" is defined as the level just below the first minimum. Specifically, the histogram is first smoothed using a running block filter. That is, for a position on the horizontal axis the vertical value on the curve is replaced by the average of the vertical value and its adjoining values. This computation is performed in steps along the horizontal axis (video level) until there are ten consecutive values for which the vertical axis increases. The "background value" is then defined as the lowest of these ten values. An "edge point" on each horizontal line is defined as the horizontal location for which the video level changes from equal to or below the "background value" to above that value or changes from above that value to equal or below that value. As the video scan proceeds, the location of each point is saved. Thus, at the end of each video frame, a set of point locations is stored in the computer memory (see FIG. 3).

Figure 7:
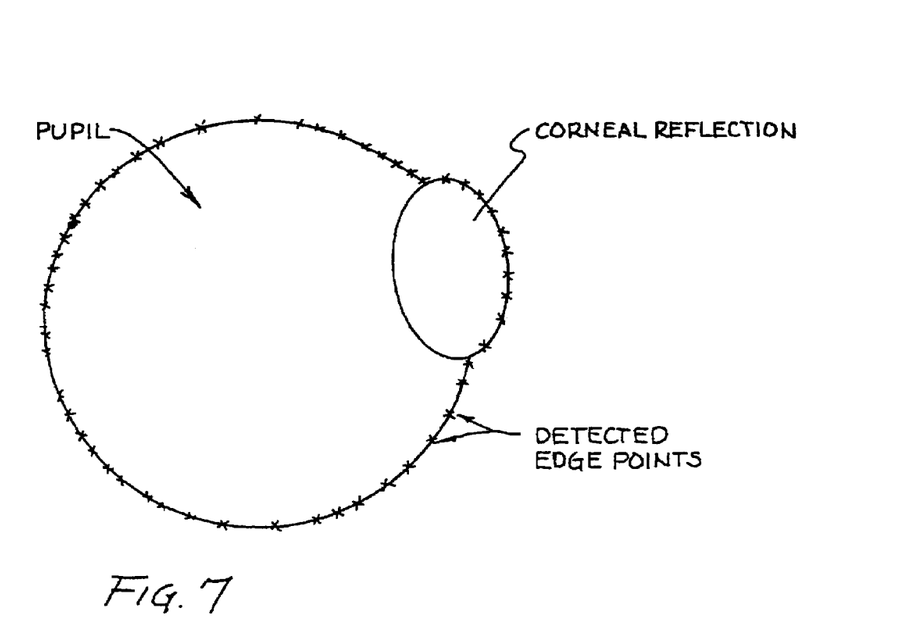
FIG. 7 illustrates determination of edge points.

If the pupil image consists solely of a bright disk on a dark background, the above described procedure would essentially always be successful in finding a close approximation to the actual pupil edges. However, for real pupil images the procedure is confounded by two sources of reflections. First, light reflected from the cornea; if this light reaches cameras $CAM_1$ and $CAM_2$, it will form a bright spot superimposed on the pupil image. If that spot were entirely within the margins of the pupil, it would not interfere with the process described above. However, if it falls on the edge of the pupil image, as it may when a patient is looking at an angle to the optical axis of the optical system, then it will appear as a bulge on the edge of the pupil, as illustrated in FIG. 7. Therefore, some of the "edge points" located by the above computations will actually be edges of the corneal reflection instead of the edge of the pupil. Second, a similar problem arises if the image of aperture A1 falls on the edge of the pupil, as it might during an eye movement too fast to be accurately tracked and compensated. In that event, finding the center and the edges of the pupil requires special procedures.

One such special procedure will described below. The edge points are collected as described above. There will typically be several hundred such points. An ellipse is then found (determined) that best fits the set of edge points. The pupil of the human eye is usually circular, but if it is viewed from an angle, as it will be if the patient is looking at a point other than on the optical axis, then the image of the pupil will approximate an ellipse. So long as the reflections from the cornea and iris do not overlap a major part of the pupil edge (and so long as the pupil is not of grossly abnormal shape), such a procedure yields a good estimate of the locations of the actual pupil center and the edge.

One method for finding the best fitting ellipse will be described. Assuming that two hundred points have been labeled edge points by the above procedure, each of such points has a horizontal (x) and a vertical (y) location. Assume that these two hundred points, that is pairs of values (x,y), are in a consecutive list. Five points are selected at random from the list, requiring only that each selected point be separated from the next selected point by at least ten positions on the list. This process will then yield the locations of five putative edge points that are some distances apart on the pupil. These five pairs of values are substituted into the equation for an ellipse and solved for the five ellipse parameters. One form of equation for an ellipse is:

$$c1*x^2 + c2*xy + c3*y^2 + c4*x + c5*y = 1$$

Substitute the five putative edge points as the pairs (x,y) of values in that equation. Invert the matrix to find the values for c1 through c5. Then the angle that the ellipse makes with the xy axis is:

$$\theta = \tfrac{1}{2} * \text{arc cot}((c1-c3)/c2)$$

Then if u=x*cos θ+y*sin θ and v=−x*sin θ+y*cos θ, then
d1*u^2+d3*v^2+d4*u+d5*v=1

Where d1=c1*cos^2+c2*cos θ*sin θ+c3*sin^2 θ

$d3=c1*\sin{^2}\theta-c2*\cos\theta*\sin\theta+c3*\cos{^2}\theta$ $d4=c4*\cos\theta+c5*\sin\theta$ $d5=-c4*\sin\theta+c5*\cos\theta$ The center of the ellipse has u coordinate u=−d4/(s*d1) and v coordinate V=−d5/(2*d3) so the center of the ellipse has the x coordinate $x=u*\cos\theta-v*\sin\theta$ and the y coordinate $y=u*\sin\theta+v*\cos\theta$ If R=1+d4^2/2d1+d5^2/2d3 then the semiaxes of the ellipse have lengths
   Square root (R/d1) and square root (R/d3)

This entire procedure is repeated, say, 100 times for 100 different sets of putative points yielding 100 different estimates of the x,y location of the center. The best fitting ellipse is the one for which the center is closest to the median x and y values of the set of 100.

The resulting deviations between the horizontal and the vertical locations of the center of the chosen ellipse and the optical axis of the optical system can be used directly as error signals to drive the positioning servos associated with assembly 20 (FIG. 1*a*) and the image of aperture A1 can be directly and finely positioned so that the image lies just inside the pupil.

Figure 2A:
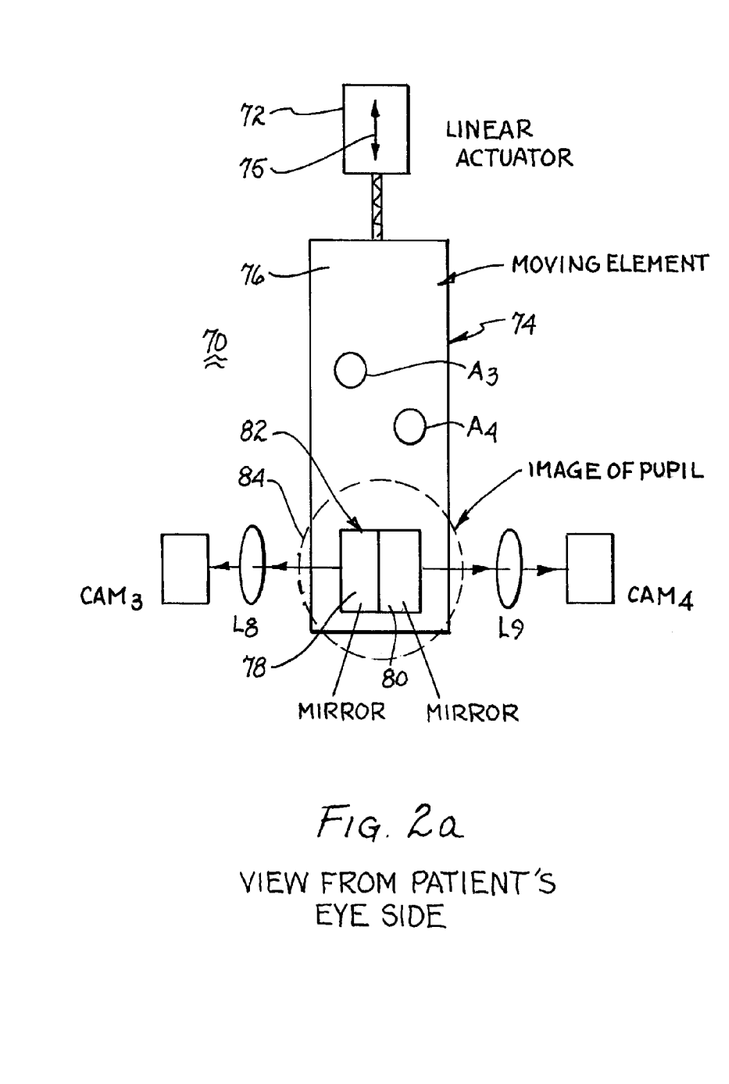
FIGS. 2A and 2B illustrate representations of the front and side views of apparatus for focusing the image.
Figure 2B:
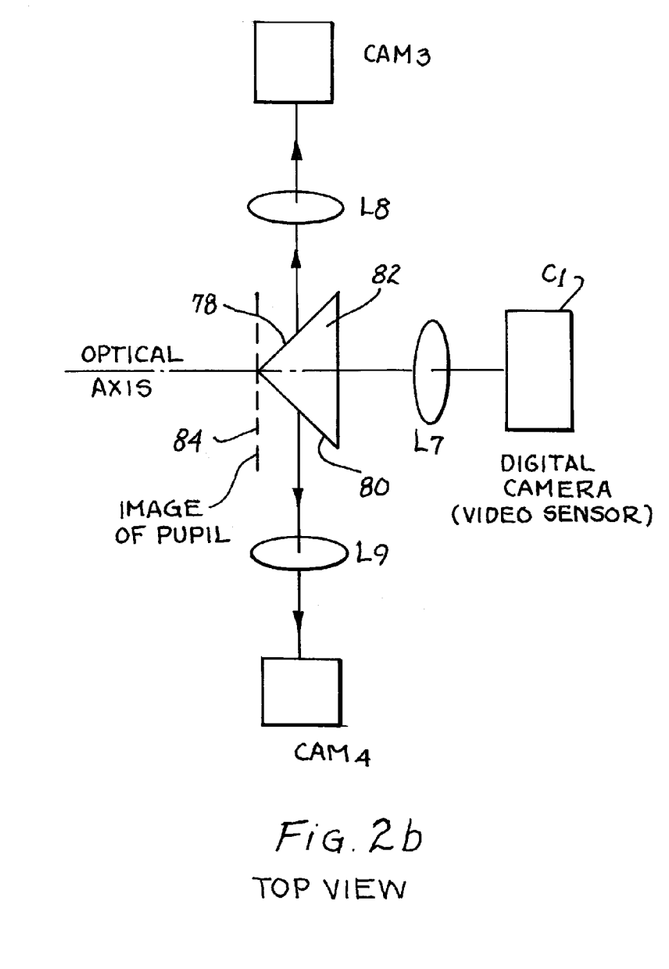

An automatic method for focusing the ftndus image will be described with reference to FIG. 2*a* and 2*b* showing an assembly 70. Aperture A3 and A4 are holes significantly smaller then the image of the pupil and which is conjugate with the pupil; that is, they are in the same plane as the image of the pupil but offset laterally and vertically. In the preferred embodiment, apertures A3, A4 are circular apertures two millimeter (2 mm) in diameter. Apertures A3 and A4 are mounted on subassembly 74 coupled to a linear actuator 72 that can move the subassembly rapidly in a vertical direction, as depicted by arrows 75. Subassembly 75 lies in the plane of A2 (see FIG. 1) and representatively identified by a box labeled 77. In the alignment method described above, the image of aperture A1 is made to lie near the edge of the pupil and a fundus image is saved. To focus, two images are saved in rapid succession, one with aperture A4 lying to the right of the center of the pupil image and the second with aperture A3 lying to the left of the center of the pupil image, by enabling linear actuator 72 to rapidly translate plate 76. If the focusing assembly FA is positioned so that the fundus image FI lies in the focal plane of lens L6 (the fundus image is thus correctly focused on video sensor C1) then the two images taken with apertures A3 and A4 in the two positions will be in registry and superimposable. However, if focusing assembly FA is not correctly positioned and the image is out of focus, then one of the images will be horizontally displaced with respect to the other. With the particular optical arrangement illustrated in FIG. 1, the direction of the displacement (unit 23, arrow 25) indicates the direction that focusing assembly FA must move to achieve correct focus and the size of that displacement is directly proportional to the distance the focusing assembly must move to correct focus.

Figure 8A:
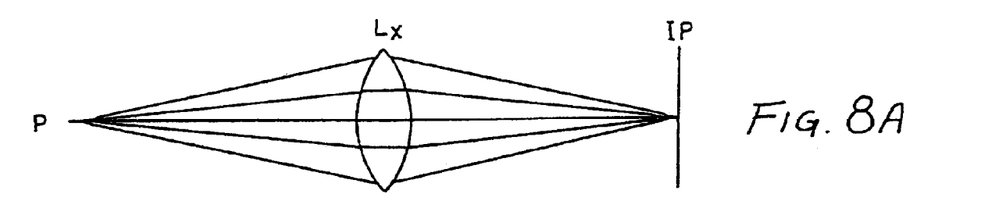
FIGS. 8A, 8B and 8C depict the light rays from a point to an image plane without an interposed aperture, and with an interposed aperture at two locations displaced from one another.
Figure 8B:
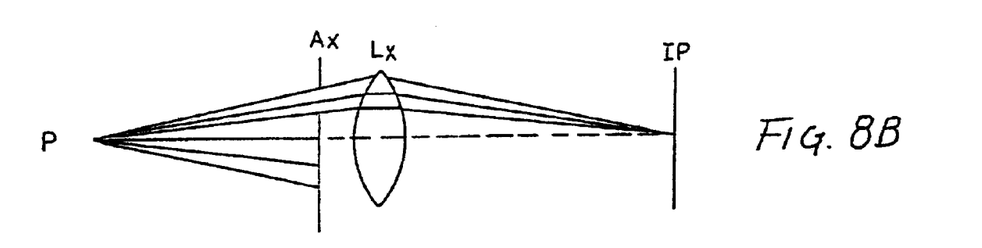
Figure 8C:
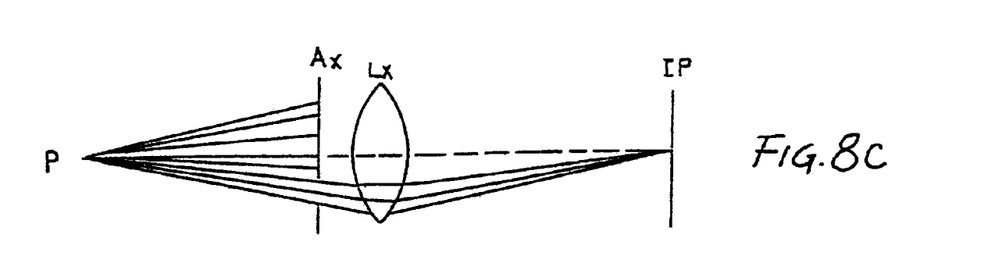
Figure 9A:
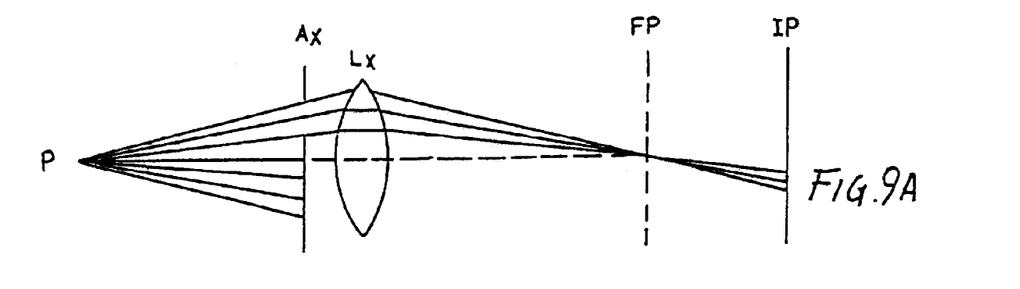
FIGS. 9A and 9B illustrate the shift of an image upon an image plane located beyond the focal plane in response to displacement of an interposed aperture from one location to another.
Figure 9B:
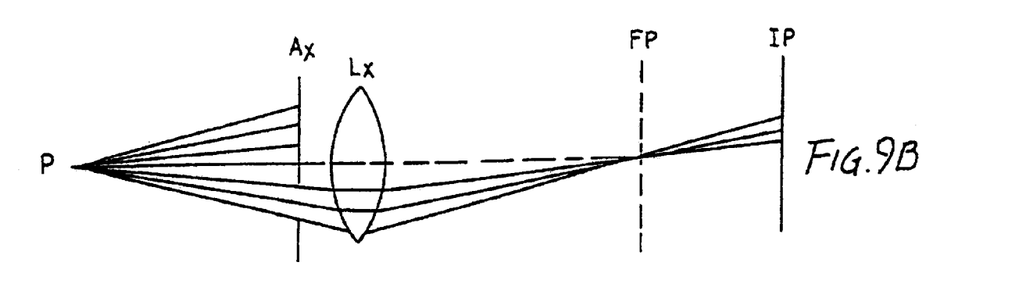
Figure 10A:
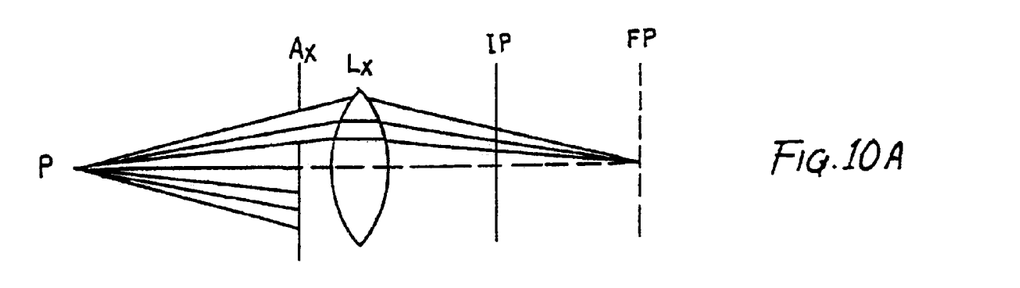
FIGS. 10A and 10B illustrate the shift of an image upon an image plane located short of the focal plane in response to displacement of an interposed aperture from one location to another.
Figure 10B:
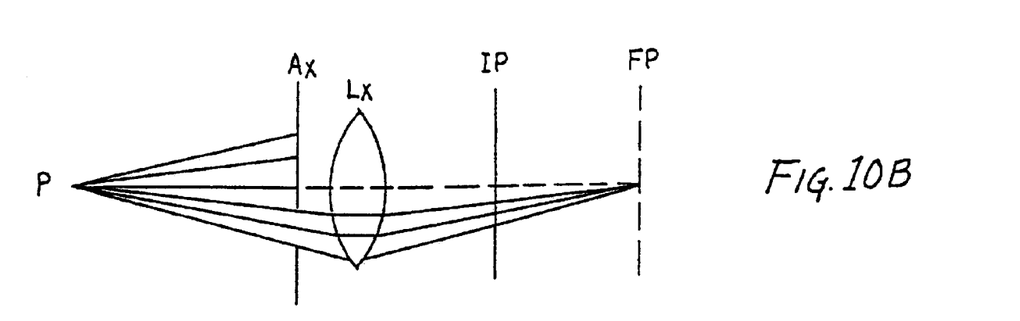
Figure 11:
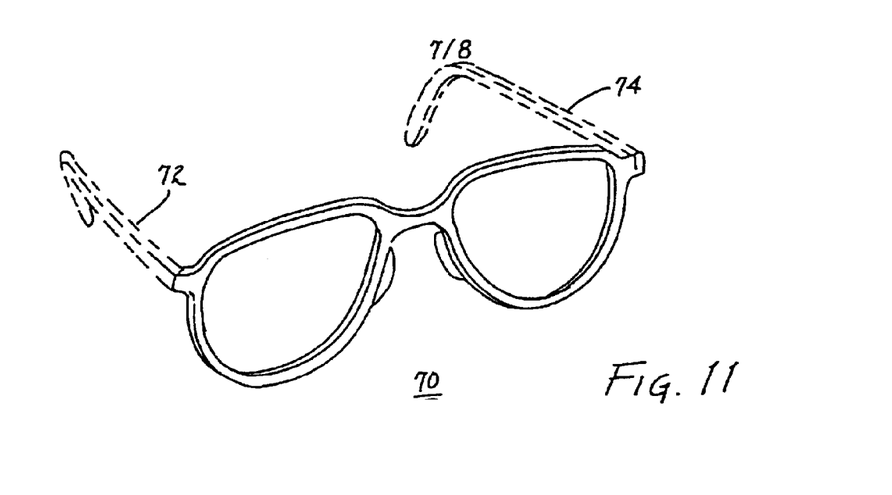
FIG. 11 illustrates a head restraint in the form of a pair of spectacles.

To explain more clearly the direction of displacement of the focusing assembly (FA) to achieve correct focus, joint reference will be made to FIGS. 8A, 8B, 8C, 9A, 9B, 10A and 10B. As shown in FIG. 8A, lens Lx forms an image of a point P that is sharply focused on image plane IP. If the aperture of an apertured plate Ax is placed between point P and lens Lx off the optical axis, the image of point P will be in focus on image plane IP, as shown in FIG. 8B. However, because certain of the-rays are excluded by the plate, the intensity of the image on the image plane will be reduced. As depicted in FIG. 8C, displacement of the aperture in apertured plate Ax will have no effect upon the location of the image of point P on the image plane. If the image plane IP is displaced from the focal plane FP, as depicted in FIG. 9A, a blurred image of point P will appear on the image plane at a location diametrically opposed relative to the optical axis from the aperture in apertured plate Ax. When the apertured plate is displaced (like the displacement shown in FIG. 8C), the blurred image on the image plane will be displaced in a direction opposite from the displacement of the apertured plate, as shown in FIG. 9B. If image plane IP is short of the focal plane FP, as shown in FIG. 10A, the rays passing through the aperture of apertured plate Ax will form a blurred image of point P on the image plane. This blurred image will be on the same side of the optical axis as is the aperture. If the apertured plate is displaced (like the displacement shown in FIG. 8C), the blurred image of point P on the image plane will be displaced in the same direction, as shown in FIG. 10B. From this analysis, the following conclusions are evident. If the image is in focus on the image plane, any shift of an apertured plate will not affect the position of the image in the image plane. If the image plane is beyond the focal plane, the image on the image plane will shift in a direction opposite to the direction of displacement of the aperture. Congruously, if the focal plane is beyond the image plane, the image on the image plane will shift in the same direction as the aperture is displaced. From these relationships, it is a simple computational exercise performable by the computer system illustrated in FIG. 3 to determine the direction and amount of displacement of focal assembly FA necessary to place the image of the fundus in focus on video screen C1.

Thereby, automatic focusing is achieved by finding the displacement of one image of a pair of images that is required to bring the two images into registry and then moving the focusing assembly in accordance with such result. The required displacement can be found by computing a cross-correlation function between the two images. This is a mathematical computation that, in effect, lays one image on top of the other, measures how well the two images correspond, then shifts one image horizontally a little with respect to the other, measures the correspondence again, shifts the one image a little more and measures the correspondence again and repeats these steps for a large number of relative positions of two images. Finally, the shift that produces the best correspondence is computed.

Even when a patient is trying to hold his/her eye steady, the eye is always moving and as a result the fundus image is continually shifting across the sensing surface of video sensor C1. Exposure durations for individual images are chosen to be short enough (about 15 milliseconds) so that this motion does not cause significant blur. Nevertheless, the time interval between members of pairs of images taken during the automatic focusing procedure may be long enough to allow movement between the images that would confound the focusing algorithm. Therefore, the actual procedure requires that a number of pairs of images be collected and, only when two members of a pair agree will they be used as the measure of focus error.

The focusing method described above requires that a number of image pairs must be collected in order to find a set that is relatively unspoiled by eye movements. It would be preferable to obtain the two images (one through the left and the other through the right side of the pupil) simultaneously, so that eye movements would not affect the result. A method for simultaneous image collection is described below.

FIG. 2A illustrates of an assembly 70 that lies approximately in the plane of aperture A2 shown in FIG. 1 and mounted on the focus assembly FA (representatively identified as box 77). FIG. 2A shows a view of assembly 70 from the patient's side of the optical system and FIG. 2B is a representative top view of the assembly. A linear actuator 72 moves a subassembly 74, as represented by arrow 75, up or down. The subassembly consists of an opaque plate 76 with two round apertures, labeled A3, A4 and a pair of mirrors 78, 80. In one position of the subassembly, one (A3) of the two apertures lies just to the left of the optical axis and in another position, the other aperture (A4) lies just to the right of the optical axis. Those are the two positions described above for collecting images through the right and left sides of the pupil.

If subassembly 74 is moved farther upward by linear actuator 72, the image of the patient's pupil will fall on double mirrors 78,80. In a preferred embodiment, the double mirrors are formed by a right angle prism 82 with the two faces (78, 80) that form a right angle being silvered. When the mirrors are in place, light from the fundus that exits through the left side of the pupil is deflected through a lens L8 and onto a video sensor or camera, $CAM_3$, and light from the right side of the pupil is deflected through another lens L9 and to another video sensor or camera, $CAM_4$. When the fundus image is in proper focus, light from the fundus will be collimated when it arrives at each of lenses L8, L9 and, because cameras $CAM_3$ and $CAM_4$ lie in the focal planes of those lenses, an image of the fundus will be formed on each camera, one of the images being formed with light passing through the left side of the pupil and the other is formed with light passing through the right side of the pupil. The two cameras are synchronized so that the two images are captured simultaneously.

If the fundus is in correct focus, and if the two lenses (L8, L9) and two cameras ($CAM_3$, $CAM_4$) are perfectly positioned on the optical axes, then the two images will occupy identical positions on the two cameras. If the image is out of focus, the two images will move in opposite directions with respect to their respective cameras. Thus, computing a cross-correlation function on the two images provides the information necessary to move the focus assembly FA to achieve correct focus, (by the same principle as explained with reference to FIGS. 8, 9 and 10). Because the two images were collected simultaneously, eye movements cannot perturb the measurement.

Figure 2C:
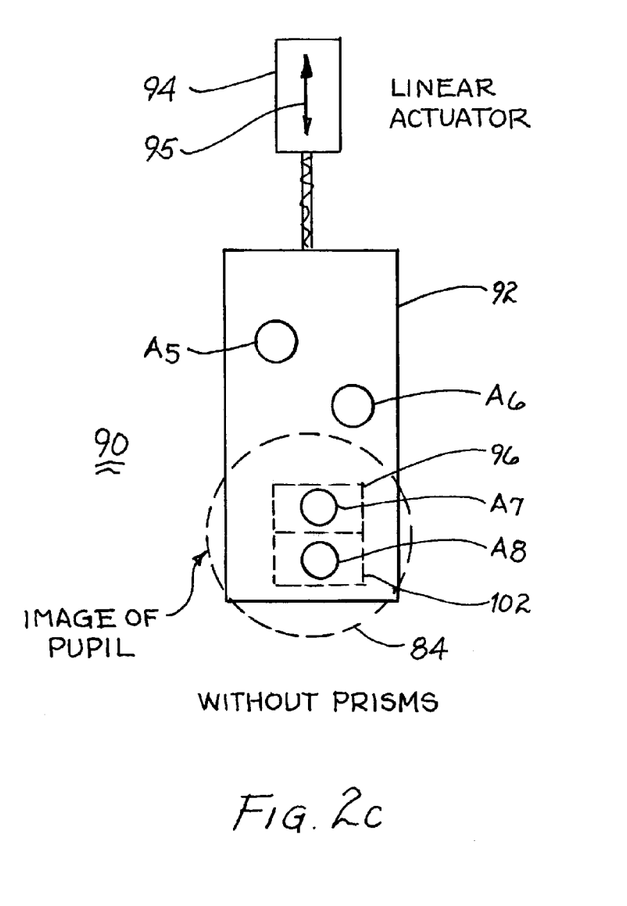
FIGS. 2C and 2D illustrate representations of the front and side views of a variant apparatus for focusing the image.
Figure 2D:
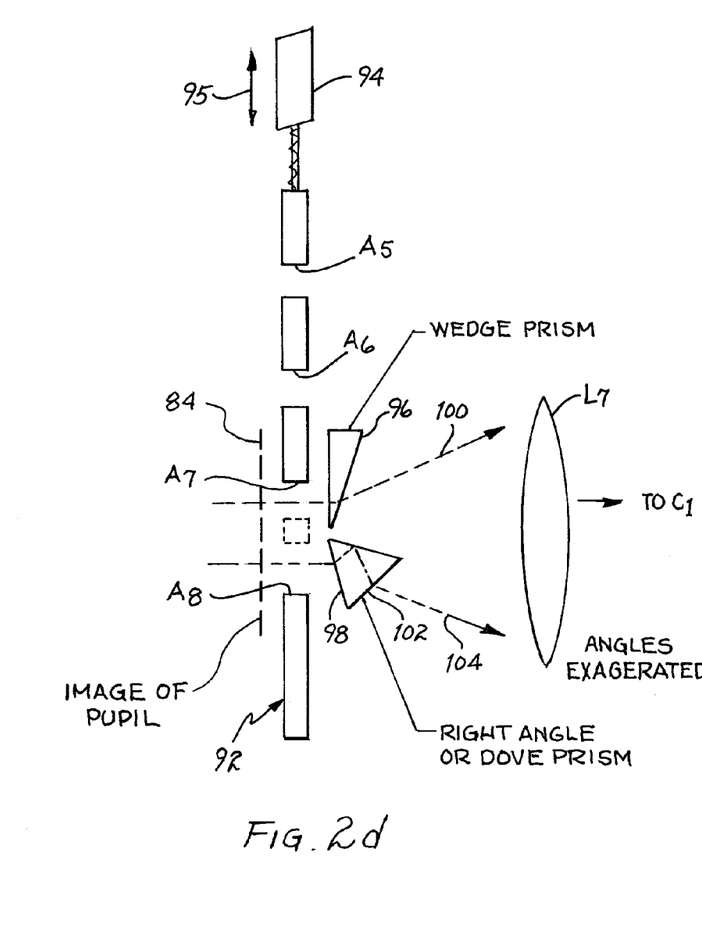

FIGS. 2C and 2D show another method for obtaining images from the two sides of the pupil simultaneously. FIG. 2C is a side view of an assembly 90 much like assembly 70 shown in FIG. 2A and is placed in the same position (box 77 in FIG. 1) in the plane of the image of the pupil. The two upper holes A5, A6 are, again, the holes for imaging the fundus through the right (A6) and left (A5) sides of the pupil for stereo imaging. When subassembly 92 is raised by linear actuator 94 (as represented by arrow 95) to cause the image of the pupil 84 to fall symmetrically on two lower holes A7, A8, one hole lets through light from the fundus that passes through the top of the pupil and the other through the bottom of the pupil. A wedge prism 96 is placed over top hole A7 and right angle prism 98 or dove prism is placed over lower hole A8, as shown in FIG. 2D. Light passing through the two holes (A7, A8) and prisms 96, 98 falls on lens L7 (shown in FIG. 1) and forms fundus images on video sensor C1.

If the prisms were removed and the fundus were in good focus, the images through the top and bottom holes would be precisely superimposed, but if the image is out of focus, one image would move up and the other down, in proportion to the degree of defocus. If that displacement could be measured, it would serve as the error signal to perform automatic focusing of the fundus image. However, because the two images would strongly overlap, there is no simple way to distinguish one image from the other. The prisms serve the function of moving the two images so that they do not overlap, as follows.

Upper wedge prism 96 deflects all of the rays 100 passing through it upwards, 15 degrees in the preferred embodiment. Therefore, the fundus image formed through the top of the pupil will move upwards on the camera. This will cause the top half of the image to fall above the sensor surface and be lost. However, the bottom half of the image will fall on the top half of the sensor and can be captured since the field of view is 30 degrees.

Right angle prism 98 acting as a dove prism, performs two different functions. First, because hypotenuse side 102 of the prism is not horizontal but is tilted downward, the image (ray 104) passing through it will be deflected downward by 15 degrees. If this were its only action, it would cause the upper half of the fundus image to fall on the lower half of the sensor. Therefore the two images, being different parts of the fundus, could not be compared. However, its dove prism action causes the image passing through it to be rotated through 180 degrees (as depicted by ray 104), so that the bottom half of the fundus image falls on the bottom half of the sensor. That allows relative positions of the two images (and thus the focus error) to be computed. In this way, the focus error can be determined from (half) images collected simultaneously.

Of course, if the two lower holes (A7, A8) were side by side instead of one above the other, and the prisms were rotated accordingly, the two half images would be positioned one on the left and the other on the right half of the sensor, and the computation for focus error could again be accomplished.

Selection of the fluids region to be imaged will now be described. Adjacent beam splitter BS1 illustrated in FIG. 1 lies a set of dots 15, 16, 17, 18 and 19. Each dot represents a visible light emitting diode (LED). Beam splitter BS1 transmits about 10% of the light from these LED's toward lens L3 and the eye. The set of dots lies in the back focal plane of lens L3 and these LED's appear to the eye as if they were a long distance away. Only one of the LED's is illuminated at any given time and the patient is asked to look at it. When the patient looks at the illuminated LED, the location of the LED with respect to the optical axis of the instrument determines the location on the fundus that will be illuminated and imaged. For example, if the LED that lies on the optical axis is turned on and the patient fixates it, then the image will be centered on the fovea or macula. If the illuminated LED is 17 degrees (17°) to the patient's left, then the region of the fundus imaged has its center 17 degrees (17°) to the left of the macula (as observed from the front of the eye).

In addition to the LED's in the plane labeled FIX, other visible LED's, such as LED 28 shown in FIG. 1, are positioned at various angular displacements from the optical axis, lying, such as to the side of lens L4. When one of these LED's is turned on, it does not appear at optical infinity but nevertheless the patient can successfully fixate it to yield a view of more peripheral fundus features.

When the operator sets up the instrument prior to collecting images, he/she selects the region or set of regions of the fundus to be imaged. If just one region is to be imaged, the appropriate LED will be lighted. If a series of locations is to be imaged, the computer (see FIG. 3) automatically selects the LED corresponding to the first location; after the image has been collected, the remaining selected LED's are lighted in sequence until the desired sequence of images has been obtained. If such a sequence involves locations that are widely separated so that the patient must make a significant eye movement to refixate, then the computer commands the horizontal and vertical positioning servo mechanisms of assembly 20 (FIG. 1a) to move optical system 10 (and optical axis) to the position where the center of the pupil is expected to be after the fixation movement.

After the image of aperture A1 has been located to exclude the corneal reflection and focusing has been achieved, another pair of images is collected with aperture A2 in each of two positions. This pair of images constitutes a stereo pair of images with a known stereo base, which base is the distance through which aperture A2 has moved.

During the alignment and focusing procedures previously described, filter F (see FIG. 1) blocks visible light but transmits near infrared wavelength radiation. To obtain an image or set of images in infrared illumination, this filter need not be changed. For certain forms of colored images, it is necessary to collect an image, change the filter to one transmitting a different wavelength band, acquire another image and return the infrared filter. The result is two or more images, each taken in a different wavelength band. To display a single color image, the different images are used to drive different color guns in a display device. For example, if one image is collected in red illumination and a second is collected in green illumination then the red image is made to drive the red gun in the display device and the green image is made to drive the green gun in the display device. The combined images will appear as a normal (two color) image.

During the interval between images collected in different wavelengths, it is possible that the eye, and thus the fundus image, will move significantly. If such movement occurs, then the variously colored images would not be in registry when displayed. To prevent this occurrence the images are automatically registered before being displayed by performing a two-dimensional cross-correlation and then shifting the images in accordance with the result.

Essentially all standard ophthalmic instruments position a patient's head using a combination of a chin rest and a forehead rest. Other devices, such as a combination of chin rest and support for the bridge of the nose would be suitable. Typically, only a bridge of the nose rest is used in the present device. These types of devices are representatively shown in FIG. 1 by box 13. The variations in the location of the eyes with respect to the bridge of the nose is such that virtually all eyes will fall within a cube that is fixed with respect to the instrument and is about 20 millimeters on a side. This is a much smaller variation then is encountered by using the usual chin and forehead rest apparatus. Thus, the commonality and uniformity of the location of the eyes with respect to the spectacles or nose bridge requires a very small range of accommodating movement of optical system 10. Furthermore, a properly chosen device constrains head movement appreciably better than a chin and forehead rest apparatus; thus, the requirement for an automatic tracking system is reduced.

The motion of focusing assembly FA (see FIG. 1) compensates for a patient's spherical refractive error (near or farsightedness) but does not correct for astigmatism. Because the fundus images are collected through a small aperture A2, moderate amounts of astigmatism will not significantly spoil the image quality. If a patient has a strong astigmatism, correction is desirable. In principle, this correction could be achieved by allowing the patient to wear his/her glasses in the instrument. However, the reflections from such eyeglasses may seriously impair the image quality. An equivalent result which does not create serious reflections is that of mounting the patient's eyeglasses in the optical system in a plane close to the plane of aperture A2 with the same orientation as when worn. A representative mounting 29 for receiving and retaining a lens of a pair of glasses is shown in dashed lines in FIG. 1.

Color images are always composed of what can be considered as separate images taken in each of a number of wavelength bands. In the present invention, the bands are. chosen by selecting filters (such as filters F, F1 shown in FIG. 1). When the fundus is illuminated with green light, the resulting images show the superficial features of the retina clearly because green light is either reflected from the superficial features or if it is not reflected, it is completely absorbed. When the fundus is illuminated with red or near infrared light, the light passes through most of the superficial features and is reflected from deeper ones. Thus, images in green light reveal some of the nerve tissue of the retina and the blood vessels that nourish those tissues, while images in red illumination reveal the subretinal (choroidal) vessels that nourish the deeper layers.

It is standard procedure in fimdus imaging to display black and white images taken in green and in red light to reveal these different features and also to combine those images to form a single color image. Through software and manipulation of a mouse a technique has been implemented that presents these images in an interesting and useful way as set forth below.

The computer screen 60 (FIG. 3) that displays the fundus image includes a mouse (48) controlled computer generated (CPU32) slider. When the slider is at one end of its travel, the red light image is displayed as a black and white image. At the other end, the green light image is displayed as a black and white image. Between those two positions, the two images are superimposed by having the red image drive the red gun of the display and the green image drive the green gun. As the slider moves from the red light end toward green light end, the intensity of the red image diminishes and the intensity of the green one increases. In this way, as the slider moves, the image changes as if the depth of the view of the fluids were changing. The selective change in image can be accomplished when viewing the images in stereo as well.

When a fundus image is displayed, a small image of the pupil that was taken at the same time as the fundus image is also displayed. The pupil image has drawn upon it indications of which parts of the pupil were used to collect the images (that is, which parts of the pupil were imaged on the two positions of holes A3, A4 or A5, A6 in FIG. 2A and 2C, respectively). In this way, the operator can judge whether or not, for example, the patient's eye lids partially obscured the optical paths, whether or not eye lashes might have interfered, etc. This is particularly useful when the fundus image appears poor, because it often informs the operator about what needs correction.

If the eye being imaged has a cataract that lies in the relevant optical path, the fundus image can be spoiled. The way in which the pupil image is formed in the cameras, (FIG. 1, CAM$_1$ and CAM$_2$) by retro-reflection from the fundus, results in cataracts being visible to the operator. If the operator observes a cataract that will spoil the image, he or she can choose a control option and use mouse 48 to move the aiming point of the alignment servos and thus move the optics with the respect to the eye to try to avoid the cataractous region.

While the invention has been described with reference to several particular embodiments thereof, those skilled in the art will be able to make the various modifications to the described embodiments of the invention without departing from the true spirit and scope of the invention. It is intended that all combinations of elements and steps which preform substantially the same function in substantially the same way to achieve the same result are within the scope of the invention.

We claim:

1. Apparatus for imaging the ocular fundus, said apparatus comprising in combination:
    a) a source of illumination for illuminating at least a section of the ocular fundus of a patient;
    b) means for directing the illumination along an optical axis to enter the pupil of the patient;
    c) at least one video sensor responsive to an image reflected from the eye of the patient for depicting the alignment of the optical axis with the pupil of the patient;
    d) positioning means for aligning the optical axis in response to the depicted alignment;
    e) a focusing assembly for focusing the image of the ocular fundus as a function of the image itself; and
    f) an image sensor for recording the focused image.

2. The apparatus as set forth in claim 1 including at least one fixed point of light upon which the patient fixates to align a section of the ocular fundus of interest with the optical axis.

3. The apparatus as set forth in claim 2 including a plurality of said fixed points of light located at separate locations to expose different sections of the ocular fundus as the patient fixates in turn upon two or more said points of light.

4. The apparatus as set forth in claim 2 including a lens for collimating the illuminating ray along the optical path entering the pupil from each of said fixed points of light to the pupil of the patient.

5. The apparatus as set forth in claim 1 including a beam splitter and an actuator for moving the illuminating light said beam splitter to move with respect to the optical axis.

6. The apparatus as set forth in claim 1 including means for rectilinearly translating said focusing assembly to focus the image of the ocular fundus on said further video sensor.

7. The apparatus as set forth in claim 1 including infrared illuminators for illuminating the eye of the patient to provide an image of the eye at said video sensor.

8. The apparatus as set forth in claim 1 including a computer system for processing the images.

9. The apparatus as set forth in claim 1 wherein said source of illumination has a wavelength in the infrared region.

10. The apparatus as set forth in claim 1 wherein said source of illumination has a wavelength in the near visible infrared region.

11. The apparatus as set forth in claim 1 wherein said source of illumination has a wavelength in the range of visible light.

12. The apparatus as set forth in claim 1 wherein said focusing assembly includes:
    a) a subassembly having a pair of holes offset in opposed directions from the optical axis; and
    b) an actuator for alternately locating one hole of said pair of holes within different regions of range of the pupil to provide respective images to said image sensor.

13. The apparatus as set forth in claim 1 wherein said focusing assembly includes:
    a) a subassembly having a pair of holes offset in opposed directions from the optical axis;
    b) an actuator for alternatively locating one hole of said pair of holes within different regions of the image of the pupil to provide respective images to said image sensor;
    c) said subassembly including a further pair of holes offset from the optical axis;
    d) said actuator being adapted to place said further pair of holes coincident with opposed regions of the image of the pupil;
    e) means for deflecting the image transmitted through one hole of said pair of further holes in a first direction;
    f) further means for deflecting and rotating 180° the image transmitted through the other hole of said pair of further holes;
    g) a lens for directing the images from said pair of further holes to said image sensor, said image sensor including means for correlating the received images to determine the focus error and for generating a signal; and
    h) said focus assembly being responsive to the signal generated by said image sensor to focus the image of the ocular fundus.

14. The apparatus as set forth in claim 13 wherein said deflecting means comprises a wedge prism.

15. The apparatus as set forth in claim 13 wherein said further deflecting means comprises a dove prism.

16. The apparatus as set forth in claim 15 wherein said deflecting means comprises a wedge prism.

17. The apparatus as set forth in claim 1 wherein said focusing assembly includes:
    a) a subassembly having a pair of mirrors for reflecting opposed parts of the image of the pupil;
    b) an actuator for translating said subassembly to place said pair of mirrors into the optical axis and cause a different region of the optical image of the pupil to impinge upon each mirror of said pair of mirrors;
    c) a first camera for recording the image of the fundus reflected by one mirror of said pair of mirrors and a second camera for recording the image of the fundus reflected by the other mirror of said pair of mirrors simultaneously with the recording of the image of the fundus by said first camera;
    d) means for correlating the images of the fundus recorded by said first and second cameras and generating a signal; and
    e) means for actuating said focusing assembly to focus the image of the ocular fundus as a function of the signal generated by said correlating means.

18. The apparatus as set forth in claim 17 wherein:
    a) said subassembly includes a pair of holes offset in opposed directions from the optical axis; and b) said actuator alternatively locating one hole of said pair of holes within different sections of the image of the pupil to provide respective images to said image sensor.

19. Apparatus for imaging the ocular fundus, said apparatus comprising in combination:
   a) a source of illumination for illuminating at least a section of the ocular fundus of a patient;
   b) means for directing the illumination along an optical axis to enter the pupil of the patient;
   c) at least one video sensor responsive to an image reflected from the eye of the patient for depicting the alignment of the optical axis with the pupil of the patient;
   d) positioning means for aligning the optical axis in response to the depicted alignment;
   e) a focusing assembly for focusing the image of the ocular fundus as a function of the image itself; and
   f) a head restraint for locating the patient's eye relative to said apparatus.

20. Apparatus for imaging the ocular fundus, said apparatus comprising in combination:
   a) a source of illumination for illuminating at least a section of the ocular fundus of a patient;
   b) at least one video sensor responsive to an image reflected from the eye of the patient for depicting the alignment of the optical axis with the pupil of the patient;
   c) positioning means for aligning the optical axis in response to the depicted alignment;
   d) a focusing assembly for focusing the image of the ocular fundus as a function of the image itself; and
   e) an image sensor for recording the focused image.

21. Apparatus for imaging the ocular fundus, said apparatus comprising in combination:
   a) a source of illumination for illuminating at least a section of the ocular fundus of a patient;
   b) means for directing the illumination along an optical axis to enter the pupil of the patient;
   c) at least one video sensor responsive to an image reflected from the eye of the patient for depicting the alignment of the optical axis with the pupil of the patient;
   d) a beam splitter and at least one lens for directing the reflected image of the ocular fundus toward said at least one video sensor;
   e) positioning means for aligning the optical axis in response to the depicted alignment;
   f) a focusing assembly for focusing the image of the ocular fundus as a function of the image itself; and
   g) an image sensor for recording the focused image.

22. Apparatus for imaging the ocular fundus, said apparatus comprising in combination:
   a) a source of illumination for illuminating at least a section of the ocular fundus of a patient;
   b) a first lens for directing the illumination through a first aperture;
   c) a filter for controlling the wavelength of the illumination emanating from said first aperture;
   d) a second lens for receiving the receiving the collected illumination and forming an image of said aperture in the pupil of the patient to illuminate a section of the ocular fundus of interest;
   e) a third and fourth lenses directing the images received from said first beam splitter upon a pair of video sensors to depict alignments; and
   f) means for relocating said apparatus in three axes in response to the images received by said pair of video sensors.

23. Apparatus for imaging the ocular fundus, said apparatus comprising in combination:
   a) a source of illumination for illuminating at least a section of the ocular fundus of a patient;
   b) means for directing the illumination off the optical axis of the pupil and to enter the pupil of the patient to reduce illumination reflected from the cornea combining with the reflected image of the fundus;
   c) a focusing assembly for focusing the reflected image of the ocular fundus as a function of the image itself; and
   d) an image sensor for recording the focused image.

* * * * *